US011156551B2

United States Patent
Schultz et al.

(10) Patent No.: US 11,156,551 B2
(45) Date of Patent: Oct. 26, 2021

(54) DEVICE AND METHOD FOR OBSERVING THE RADIATION BACKSCATTERED BY AN OBJECT

(71) Applicants: COMMISSARIAT A L'ENERGIE ATOMIQUE ET AUX ENERGIES ALTERNATIVES, Paris (FR); INTELLIGENCE ARTIFICIELLE APPLICATIONS, Montpellier (FR)

(72) Inventors: Emmanuelle Schultz, Saint Egreve (FR); Damien Decq, Grenoble (FR); Michel Roch, Saint Bres (FR); Selimen Benahmed, Grenoble (FR)

(73) Assignees: COMMISSARIAT A L'ENERGIE ATOMIQUE ET AUX ENERGIES ALTERNATIVES, Paris (FR); INTELLIGENCE ARTIFICIELLE APPLICATIONS, Montpellier (FR)

( * ) Notice: Subject to any disclaimer, the term of this patent is extended or adjusted under 35 U.S.C. 154(b) by 88 days.

(21) Appl. No.: 16/473,512

(22) PCT Filed: Dec. 21, 2017

(86) PCT No.: PCT/FR2017/053768
§ 371 (c)(1),
(2) Date: Jun. 25, 2019

(87) PCT Pub. No.: WO2018/122504
PCT Pub. Date: Jul. 5, 2018

(65) Prior Publication Data
US 2019/0339199 A1    Nov. 7, 2019

(30) Foreign Application Priority Data
Dec. 26, 2016  (FR) ...................... 1663396

(51) Int. Cl.
*G01N 21/47*     (2006.01)
*G02B 21/08*     (2006.01)
(Continued)

(52) U.S. Cl.
CPC ....... *G01N 21/474* (2013.01); *G01N 21/4788* (2013.01); *G01N 21/63* (2013.01);
(Continued)

(58) Field of Classification Search
None
See application file for complete search history.

(56) References Cited

U.S. PATENT DOCUMENTS 4,555,635 A * 11/1985 Yoshida ............... G01N 21/952
    250/559.07
4,867,530 A *  9/1989 Sedlmayr ................ G02B 6/04
    385/116
(Continued)

FOREIGN PATENT DOCUMENTS

| EP | 3 054 281 A1 | 8/2016 |
| WO | WO 2007/020554 A1 | 2/2007 |
| WO | WO 2016/054408 A2 | 4/2016 |

OTHER PUBLICATIONS

International Search Report dated Apr. 5, 2018 in PCT/ FR2017/053769, 3 pages.
(Continued)

*Primary Examiner* — Kara E. Geisel
*Assistant Examiner* — Jarreas C Underwood
(74) *Attorney, Agent, or Firm* — Oblon, McClelland, Maier & Neustadt, L.L.P.

(57) ABSTRACT

A device and method for observing an object, in particular a biological object includes a light source able to illuminate a sample. Under the effect of the illumination, the object emits back-scattered radiation that propagates to a screen,
(Continued)

the area of which is larger than 100 cm². The projection of the back-scattered radiation onto the screen forms an image representative of the back-scattered radiation, called a scattergram. An image sensor allows an image representative of the scattergram formed on the screen to be acquired.

21 Claims, 8 Drawing Sheets

(51) Int. Cl.
*G01N 21/88* (2006.01)
*G01N 21/63* (2006.01)

(52) U.S. Cl.
CPC ... *G02B 21/086* (2013.01); *G01N 2021/4759* (2013.01); *G01N 2021/8819* (2013.01)

(56) References Cited

U.S. PATENT DOCUMENTS

| | | | | |
|---|---|---|---|---|
| 5,241,369 | A * | 8/1993 | McNeil | G01B 11/303 356/445 |
| 5,327,229 | A * | 7/1994 | Konno | H04N 9/312 348/742 |
| 5,528,422 | A * | 6/1996 | Roberts | B60Q 1/2665 359/583 |
| 5,912,741 | A * | 6/1999 | Carter | G01N 21/4738 356/445 |
| 5,963,335 | A * | 10/1999 | Boutelle | G01N 21/59 356/39 |
| 7,649,628 | B2 * | 1/2010 | Wadman | G01N 21/4738 356/445 |
| 7,872,754 | B2 * | 1/2011 | Wadman | G01N 21/49 356/445 |
| 2002/0072026 | A1 * | 6/2002 | Lynam | B60R 1/082 432/77 |
| 2004/0190008 | A1 * | 9/2004 | Mieher | G01N 21/95607 356/625 |
| 2007/0146703 | A1 | 6/2007 | Adams et al. | |
| 2008/0192258 | A1 | 8/2008 | Wadman | |
| 2016/0139497 | A1 * | 5/2016 | Usukura | G03B 21/62 353/20 |
| 2017/0219485 | A1 | 8/2017 | Bae et al. | |

OTHER PUBLICATIONS

International Search Report dated Apr. 9, 2018, in PCT/FR2017/053768 filed on Dec. 21, 2017.
Kim, H. et al., "Reflected scatterometry for noninvasive interrogation of bacterial colonies", Journal of Biomedical Optics, vol. 21, No. 10, Oct. 2016, 10 pages, XP060075145.
Bae, E. et al., "Label-free light-scattering sensors for high throughput screening of microbes in food", In: High Throughput Screening for Food Safety Assessment, Biosensor Technologies, Hyperspectral Imaging and Practical Applications, Woodhead Publishing Series in Food Science, Technology and Nutrition, No. 262, 2015, 16 pages, XP055404709.

* cited by examiner

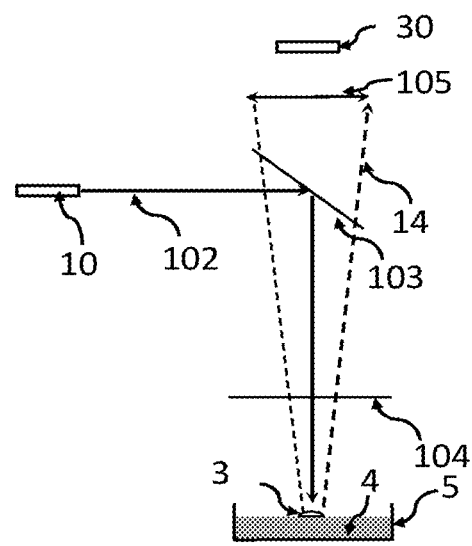
Fig. 1A
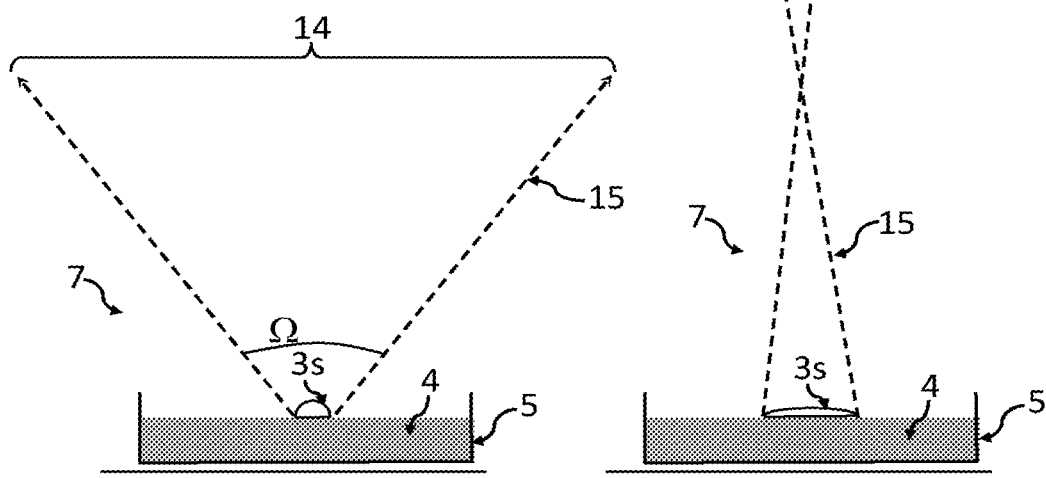
Fig. 1B                    Fig. 1C

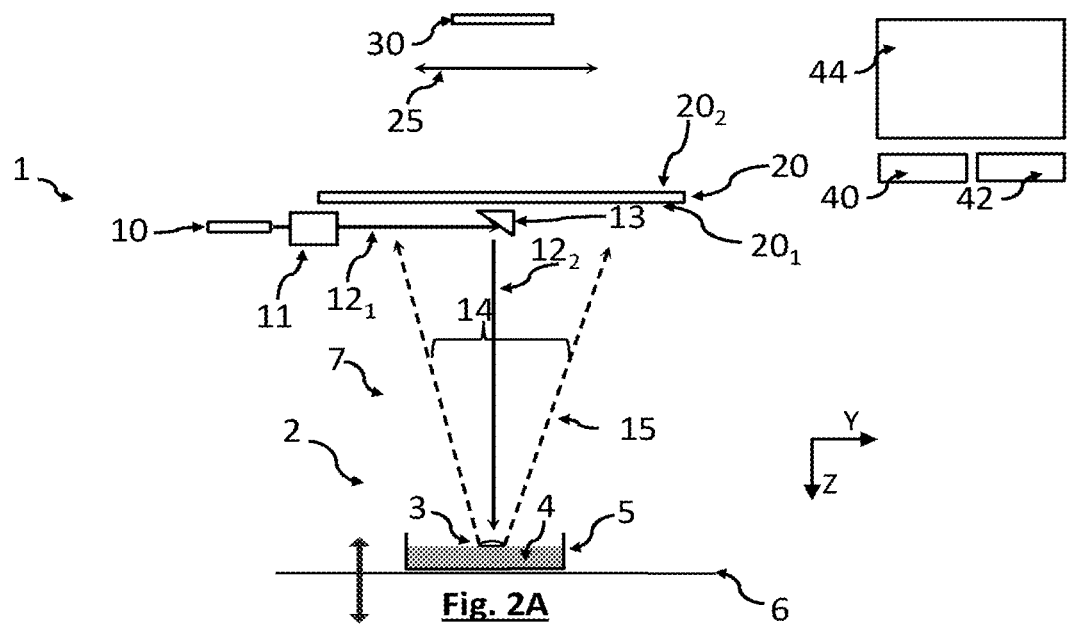
Fig. 2A
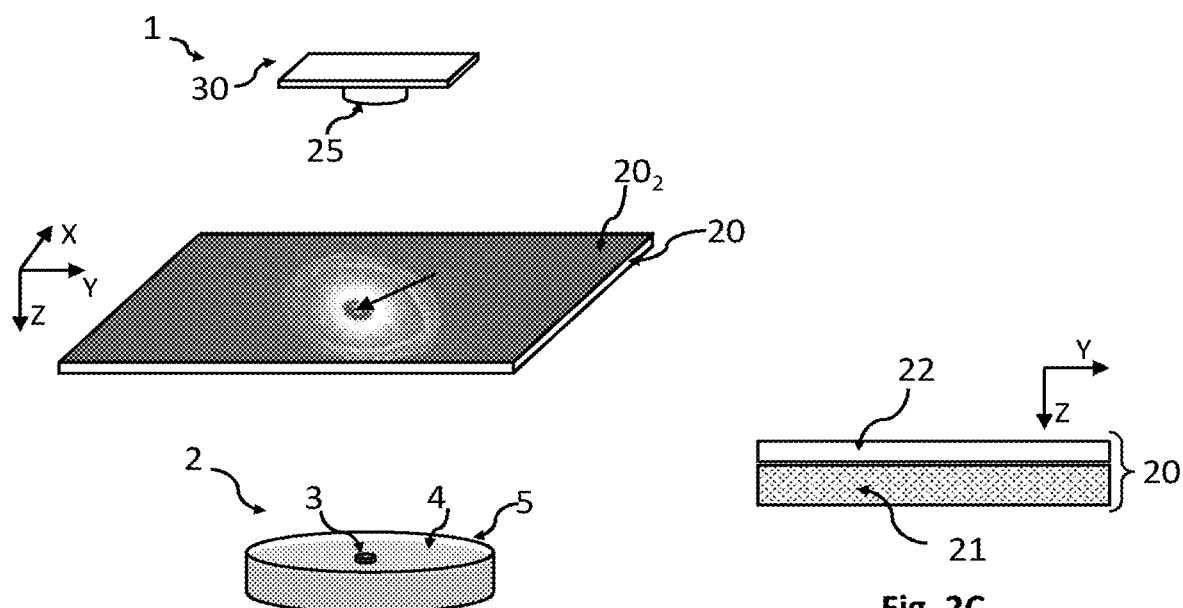
Fig. 2B
Fig. 2C

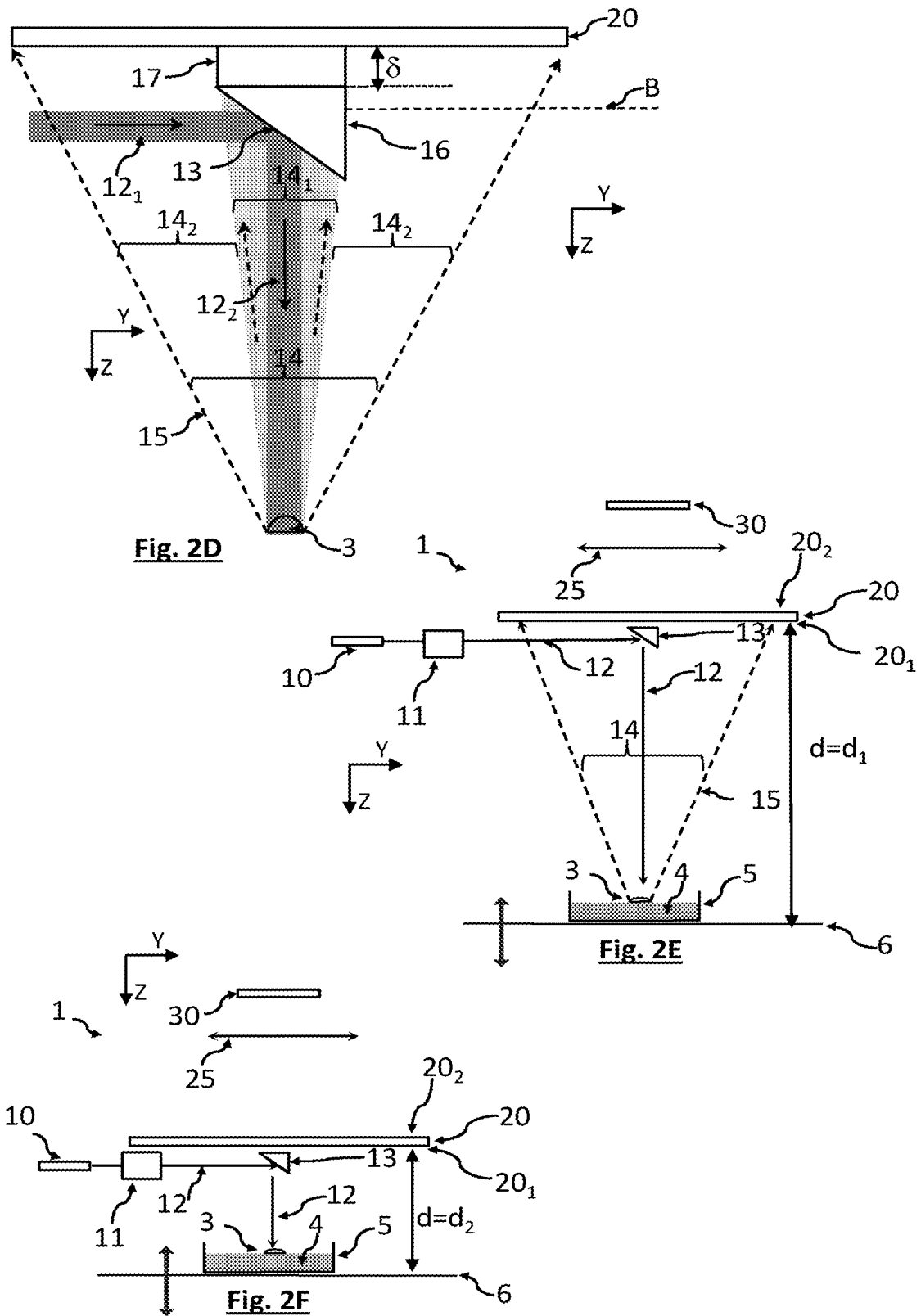

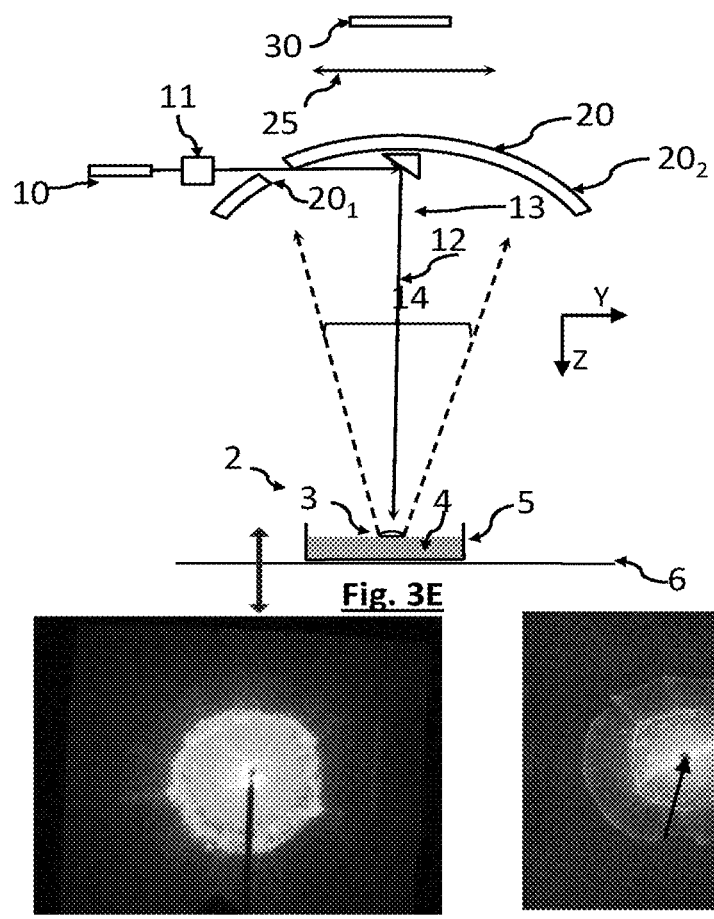
Fig. 3E
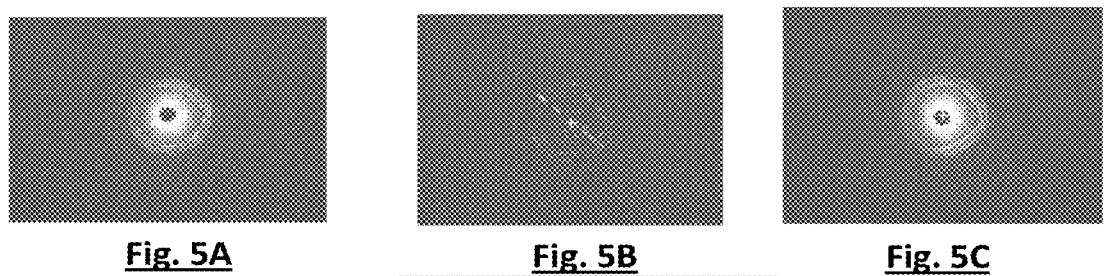
Fig. 4A  Fig. 4B
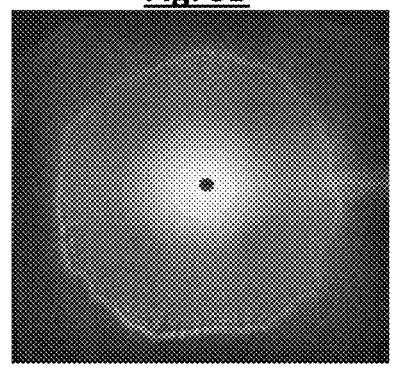
Fig. 5A  Fig. 5B  Fig. 5C
Fig. 6

DEVICE AND METHOD FOR OBSERVING THE RADIATION BACKSCATTERED BY AN OBJECT

TECHNICAL FIELD

The technical field of the invention is the observation and identification of an object, notably a biological object, in particular a bacterial colony, on the basis of an image of radiation back scattered by the object.

PRIOR ART

The identification of microorganisms, in particular bacteria, is a need that regards various fields. In the field of diagnostics, for example, the identification of bacteria allows the nature of the pathogens that are the root cause of an infection to be known, and the treatment of a patient to be optimized. Moreover, bacterial identification is a fundamental technique in epidemiology or in the fight against nosocomial infections. Beyond the health field, there are possible applications in, non-exhaustively, the hygiene, safety and food-processing fields.

Currently there are a variety of effective instruments allowing such an identification. The methods employed are in particular mass spectrometry, Raman spectroscopy, colorimetric tests, morphological analysis of colonies, or nucleic-acid amplification techniques. Methods employing a spectrometric or spectroscopic technique (mass spectrometry or Raman spectroscopy) require expensive apparatus and qualified operators. Colorimetric methods are simpler, but generally slower. As regards the amplification of nucleic acids, it requires many steps to be carried out in series while precise operating conditions are met.

The U.S. Pat. No. 74,665,560 describes a method allowing a microorganism to be characterized based on the exploitation of the scatter and diffraction, by the microorganism, of an incident laser beam. The microorganism is placed between a laser light source and an image sensor. Under the effect of an illumination by the laser beam, images are acquired in which diffraction patterns appear, the latter forming a signature of the observed microorganism. The U.S. Pat. No. 8,787,633 describes a method meeting the same objective. These documents describe a method for identifying bacteria that seems promising, but it becomes inapplicable if the medium in which the bacteria are placed is opaque, colored or scattering. Specifically, these methods use an image formed in a so-called transmission configuration, in which the sample is placed between a light source and an image sensor. If an exploitable image is to be obtained then the sample must be sufficiently transparent. Thus, this method is not compatible with samples comprising a colored culture medium, for example the medium known as Columbia blood agar (CBA), which contains Columbia agar in sheep blood. It is also not applicable to a scattering medium such as cystine lactose electrolyte deficient (CLED) agar, or to an opaque medium such as chocolate agar. However, such culture media are frequently used in clinical diagnostics.

Patent application WO2016/097063 partially addresses this problem, by proposing a method for observing microorganisms in which an image is formed not in a transmission configuration, but in a back-scatter configuration. The sample is illuminated by a laser beam. The back-scattered radiation is focused, by a collecting optic, onto an image sensor. Document WO2016/054408 describes a similar configuration, the back-scattered radiation being collected by a CMOS image sensor the active area of which may be as much as 17.28 $cm^2$.

The publication by Kim Huisung et al. "Reflected scatterometry for non-invasive interrogation of bacterial colonies", International society for optical engineering, SPIE, vol. 21, no. 10, October 2016, also describes a device operating in a back-scatter configuration. In this configuration, a planar screen is placed between the sample and an image sensor. The screen allows rear projection of the radiation back scattered by the sample. The latter is illuminated by a laser beam, which is reflected by a reflective plate before reaching the sample. The area of the reflective plate is 25 $cm^2$. The use of a translucent screen is also described in U.S. Pat. No. 5,241,369.

The inventors have implemented the method described in WO2016/097063 and have observed certain limitations, which are described below.

The objective of the invention is to overcome these limitations, by proposing a method for observing and characterizing microorganisms in a back-scatter configuration. The invention is particularly suitable for an opaque sample, while naturally remaining applicable to transparent samples. It allows colonies of microorganisms to be observed and characterized at various stages of development, independently of whether it is a question of microcolonies or macrocolonies. Another advantage is that it is simple to implement and robust, and does not require expensive instrumentation. Moreover, the method implemented is non-destructive. It may be applied to a colony, in its culture medium, without sampling being required. Lastly, the analysis is rapid, taking about one second.

SUMMARY OF THE INVENTION

The invention firstly relates to a device for observing an object, present in a sample, comprising:
  a holder, able to receive the sample;
  a light source, able to emit a light beam, called the incident light beam, in order to illuminate the object;
  an image sensor, for acquiring an image representative of radiation back scattered by the object under the effect of an illumination by the incident light beam;
the device being characterized in that it comprises:
  a screen, lying facing the holder, so as to be exposed to radiation back scattered by the object when the latter is illuminated by the incident light beam, so as to form, on the screen, an image, called a scattergram, representative of the back-scattered radiation;
  the screen comprising a first face, exposed to the back-scattered radiation;
  the image sensor being configured to acquire an image of the scattergram formed on the screen.

The light source may notably be a laser light source. The device may comprise a collimating optic, so that the light beam emitted by the light source is collimated. The device may comprise a beam-expanding optic, so as to adjust the diameter of the light beam to the size and morphology of the analyzed object.

The object may be a colony of microorganisms, for example a bacterial colony, in which case the screen allows a scattergram to be obtained the size of which is sufficiently large to characterize a colony at a sufficiently advanced stage of development.

According to one embodiment, the area of the first face of the screen is larger than 100 $cm^2$.

The device may comprise a reflective element, which is placed between the screen and the object, and which is able to reflect a portion of the incident light beam along an axis of incidence perpendicular or substantially perpendicular to the plane of the sample, the reflective element being securely fastened to the first face of the screen. This makes it possible to avoid disruption of the scattergram formed on the screen by an arm, bearing the reflective element, extending transversely to the back-scattered radiation.

The device may comprise any one of the features described below, alone or in technically producible combinations:

- The screen comprises a second face, so that the scattergram formed on the first face appears on the second face; the screen then lies between the image sensor and the holder, such that the image sensor is coupled to the second face by a focusing optic. The screen then acts as a backlit screen, transmitting the scattergram, which is projected onto the first face, to the second face.
- The distance between the reflective element and the screen is smaller than 2 cm.
- The area of the reflective element is smaller than 4 $cm^2$ or than 2 $cm^2$ or than 1 $cm^2$.
- The device comprises a binding medium lying between the reflective element and the screen, the binding medium allowing the reflective element to be fastened to the screen, the device being such that the reflective element and/or the binding medium are configured to absorb at least 20%, or even at least 30%, or even at least 50% of the back-scattered radiation propagating between the object and the screen.
- The screen is translucent.
- The screen comprises a light guide, for example an optical fiber, for conveying light between the first face and the second face. The screen may comprise a plurality of optical fibers extending between the first face and the second face.
- The screen is a photosensitive portion of the image sensor, the photosensitive portion allowing the back-scattered radiation to be converted into charge carriers.
- The screen transmits less than 90% of the back-scattered radiation from the first face to the second face.
- The screen is movable with respect to the holder, the distance between the holder and the screen being able to be adjusted.
- The incident light beam propagates between the reflective element and the object about an axis called the axis of incidence, the device comprising what is called an annular reflector, lying around the axis of incidence, between the sample and the screen, the annular reflector being able to reflect some of the radiation back scattered toward the screen.
- The screen is curved, notably toward the sample (or the object).

Another subject of the invention is a method for observing an object present in a sample, the sample lying facing a screen comprising a first face, the method comprising the following steps:

a) illuminating the object using an incident light beam emitted by a light source, the incident light beam propagating to the object;

b) exposing a first face of a screen to light radiation back scattered by the sample, under the effect of the illumination, so as to form, on said first face, an image, called a scattergram, representative of said back-scattered radiation;

c) acquiring an image of the scattergram, formed on the screen, with an image sensor.

According to one embodiment, the device comprises a reflective element placed between the screen and the object, the reflective element directing all or some of the incident light beam, emitted by the source, toward the object. The reflective element may notably be joined to the first face of the screen.

The method may comprise any one of the features described below, alone or in technically producible combinations:

- the area of the reflective element is smaller than 5 $cm^2$, or than 2 $cm^2$, or than 1 $cm^2$.
- The screen is curved, and notably curves toward the sample.
- The screen is translucent.
- The screen comprises at least one light guide, notably an optical fiber, extending between the first face and the second face.
- One face of the screen is structured so as to form a lens.
- The screen transmits less than 95% or 90% of the back-scattered radiation.
- The screen comprises a second face, the screen lying between the image sensor and the sample, such that the image sensor is optically coupled to the second face by a focusing optic, the screen being such that the scattergram formed on the first face appears on the second face.
- The method comprises, following step c), a step of adjusting the distance between the sample and the screen depending on the image acquired by the image sensor, steps a) to c) being repeated after the adjustment of said distance.
- The method comprises a step d) of characterizing the object on the basis of the image acquired by the image sensor, or on the basis of the resulting image. The characterization of the image may comprise:
    determining characteristics of the image;
    identifying the object using said characteristics and calibration characteristics established by implementing steps a) to c) of the method on a standard sample.
- The object comprises a microorganism. The object may notably comprise a plurality of microorganisms forming a colony. The object may be a bacterial colony.
- The method is implemented with a device such as described in the patent application.

Other advantages and features will become more clearly apparent from the following description of particular embodiments of the invention, which are given by way of nonlimiting example, and shown in the figures listed below.

FIGURES

FIG. 1A shows a device for observing microorganisms according to the prior art.

FIGS. 1B and 1C illustrate spatial distributions of back-scattered radiation emanating from two different objects, respectively.

FIGS. 2A and 2B show a first embodiment of the invention.

FIG. 2C shows an example of a screen able to be implemented in the first, second or third embodiment.

FIG. 2D is a detail of FIG. 2A.

FIGS. 2E and 2F illustrate a variation in the distance between the screen and the sample.

FIG. 3E shows a variant in which the screen is curved.

FIGS. 4A and 4B show a scattergram of a bacterial colony, in two different arrangements of the device.

FIGS. 5A, 5B and 5C illustrate a method for moving an observed bacterial colony so as to center it with respect to the incident light beam and to the screen. FIG. 5A is a slightly off-center scattergram. FIG. 5B results from the application of a filter to the scattergram shown in FIG. 5A. FIG. 5C shows the scattergram of FIG. 5A after recentering.

FIG. 6 illustrates one embodiment, said to be of high-dynamic range, in which various images are combined.

FIGS. 7A, 7B, 7C, 7D, 7E and 7F show scattergrams of various types of bacterial colonies.

Figure 8A:
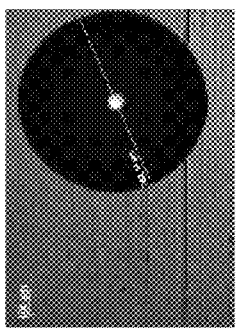
Figure 8B:
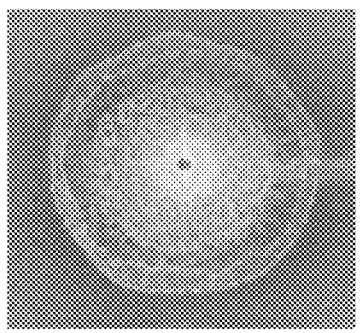

FIGS. 8A and 8B show a micrograph and a scattergram of a bacterial colony.

Figure 8C:
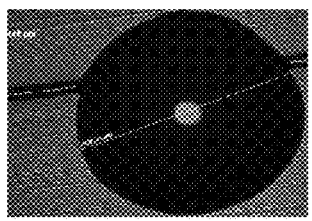
Figure 8D:
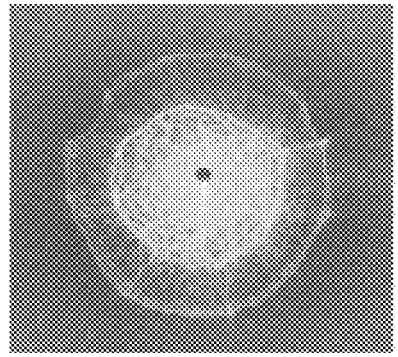

FIGS. 8C and 8D show a micrograph and a scattergram of another bacterial colony.

Figure 9A:
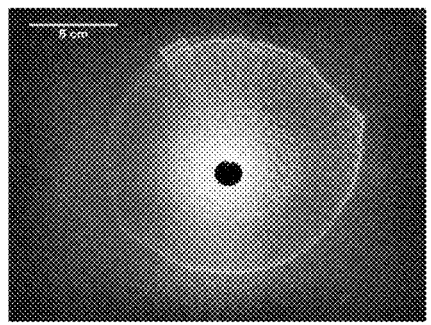
Figure 9B:
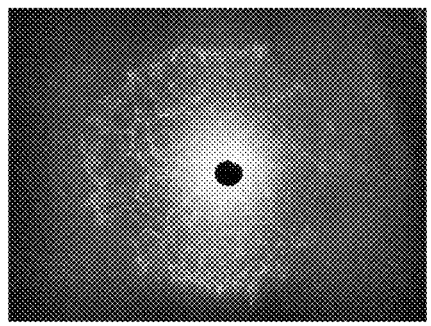
Figure 9C:
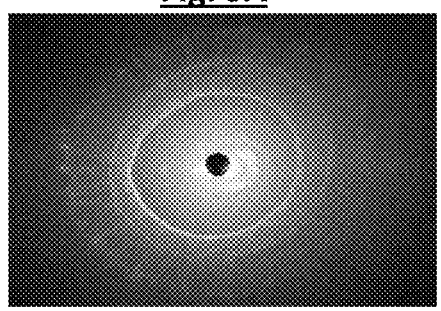

FIGS. 9A, 9B and 9C are scattergrams of bacterial colonies formed on various culture media.

Figure 9D:
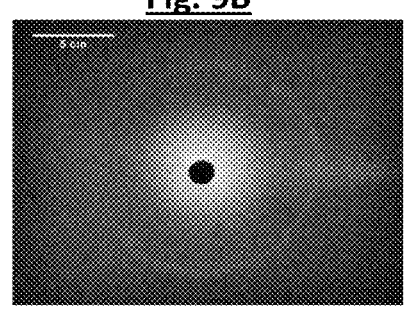

FIG. 9D shows the scattergram of a bacterial colony formed on a lawn of bacteria different from those forming the observed bacterial colony.

Figure 10:
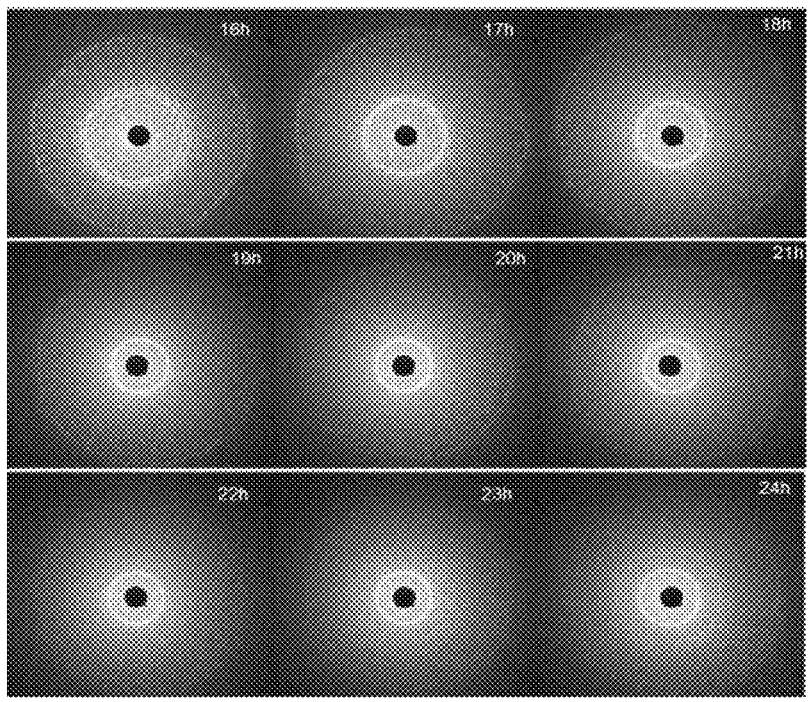

FIG. 10 shows the change over time in a scattergram corresponding to a given bacterial colony.

Figure 11A:
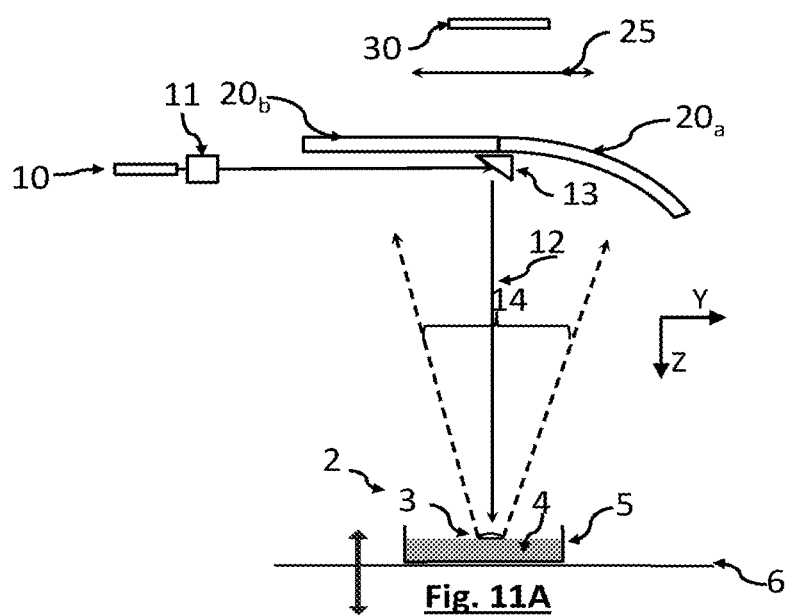

FIG. 11A shows an experimental device combining a flat screen and a curved screen.

Figure 11B:
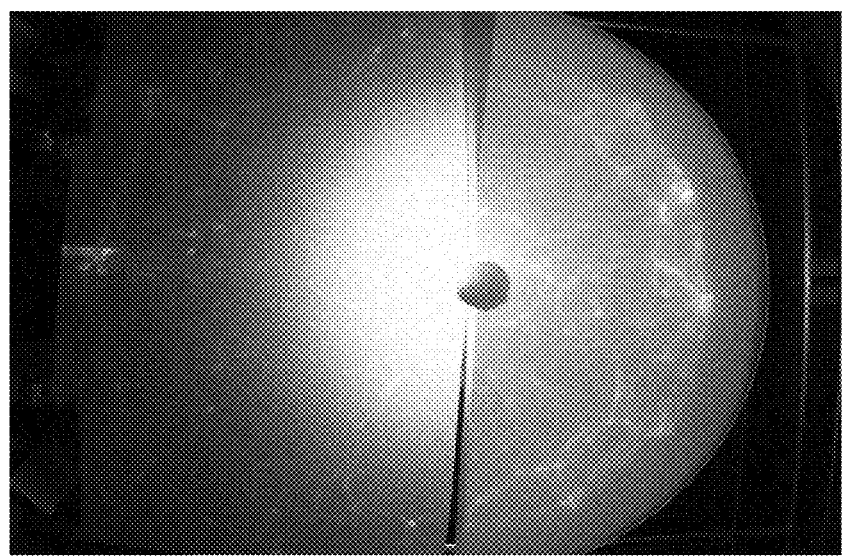

FIG. 11B is an image of a bacterial colony observed using the device schematically shown in FIG. 11A.

DESCRIPTION OF PARTICULAR EMBODIMENTS

FIG. 1A shows a device for observing microorganisms such as described in patent application WO2016/097063. A source 10 of laser light emits a rectilinearly polarized light beam 102 that propagates to an object 3 to be characterized, for example a bacterial colony placed on the surface of a culture medium 4. Before reaching the bacterial colony 3, the polarized light beam 102 is deviated by a half-silvered mirror 103, so as to propagate in a direction, called the direction of incidence, substantially perpendicular to the surface of the culture medium 4. The light beam 102 passes through a quarter-wave plate 104 before reaching the bacterial colony 3. The light beam 102 interacts with the bacterial colony 3, this resulting in the formation of back-scattered radiation 14 that propagates in a direction substantially opposite to the direction of incidence. The back-scattered radiation 14 is formed by multiple interactions of the light beam 102 with the colony 3, combining the effects of diffraction and elastic scattering in the colony. The back-scattered radiation 14 passes through the quarter-wave plate 104, then the half-silvered mirror 103, before being focused by an optical system 107 toward an image sensor 30. The image formed on the image sensor, which is called a scattergram, is representative of the back-scattered radiation 14. The scattergram may be considered a signature of the bacterial colony, allowing the bacteria forming the colony to be identified. This device, which is representative of the prior art, has been implemented by the inventors. The latter have shown that this device does not allow certain bacterial colonies to be satisfactorily observed.

Specifically, the back-scattered radiation 14 is emitted in an angular range that varies depending on the type of microorganism observed. Certain bacterial colonies, for example a colony of *Staphylococcus*, develop by gradually forming an external surface 3s having a shape close to a hemisphere bounded by an ambient medium 7, for example air. Such a case is illustrated in FIG. 1B. In this type of configuration, the back-scattered radiation 14 is divergent, and forms a cone 15 covering a high angular range Ω. By high, what is meant is comprising angles larger than 65° or even than 85°. This is notably due to the refraction of the back-scattered radiation when it crosses the surface 3s in order to be refracted in the ambient medium 7. In contrast, as shown in FIG. 1C, other bacterial colonies develop by gradually forming a planar surface 3s, the radius of curvature of which is high. Thus, the back-scattered radiation 14 is refracted in the ambient medium 7 and propagates through the latter in a convergent beam, forming a cone 15, of apex angle Ω. Bacteria of Enterobacteriaceae type form colonies having such a morphology. Thus, depending on the type of observed microorganisms and their stage of development, the morphology of a colony varies, affecting the spatial distribution of the back-scattered radiation 14. One limit of the device described in WO2016/097063 is that the field of view is small and fixed, making it unsuitable for bacterial colonies the shape of which is similar to that of the example of FIG. 1B. The inventors have defined an observing device taking into account the variability of the spatial distribution of the back-scattered radiation 14. More precisely, the device, according to the invention, has a field of view that may be adapted to the observed microorganism. Specifically, the inventors have established that for microorganisms that generate back-scattered radiation the spatial distribution of which is illustrated in FIG. 1B, a very large field of view may be necessary.

FIG. 2A shows a first embodiment of a device 1 according to the invention. In this case, this is a preferred embodiment. The device comprises a light source 10, able to emit a light beam 12, called the incident beam, that propagates to a sample 2 comprising an object 3 to be characterized. The light source 10 is preferably temporally and spatially coherent. The light source 10 is preferably a laser source. According to one variant, the light source may be a light-emitting diode or a white light source. It is then preferable for the light source to be sufficiently point-like to be spatially coherent. This may be obtained by associating the light source 10 with a spatial filter, for example a diaphragm, or an optical fiber. The light source 10 may also be associated with a bandpass filter, so as to obtain a sufficiently narrow emission spectral band Δλ, preferably one narrower than 50 nm or even than 10 nm.

The incident beam 12 emitted by the light source and that propagates toward the object 3 is preferably a parallel beam, the diameter of which may advantageously be adjusted. The diameter of the incident beam 12 is preferably comprised between 100 μm and 10 mm. The adjustment of the diameter allows allowance to be made for the size of the object 3 to be characterized. Thus, when the object 3 is a bacterial colony, this allows the size of the incident beam 12 to be adjusted to the morphology of the colony, the latter depending on the type of bacteria and on the stage of development. A forming optical system 11 may be placed between the light source 10 and the object 3. The forming optical system 11 may allow the diameter of the incident beam 12 to be adjusted. It may also allow the uniformity of a spatial distribution of the energy in the incident beam 12 to be increased, so that the light intensity in the beam is more uniform.

The object to be characterized 3 may be a microorganism or a set of microorganisms forming a colony. The microorganism may be a bacteria, a yeast, a fungus or a microalgae. The object to be characterized may also be a group of cells, forming for example a cluster. The object to be characterized may make contact with a culture medium 4, either being placed in the latter or on the surface of the latter. The culture medium 4 is confined in an enclosure 5. The culture medium 4 and/or the enclosure 5 may be opaque or translucent. In particular, it is not necessary for the culture medium 4 and the enclosure 5 to be transparent, which is a condition of the methods based on transmission configurations described with respect to the prior art. The assembly formed by the enclosure 5, the culture medium 4 and the object 3 forms the sample 2, the latter resting on a holder 6. In the example shown, the holder is a planar stage that is translationally movable along an axis Z, called the axis of incidence. The invention is particularly suitable for samples comprising an opaque culture medium 4. When the culture medium 4 is not sufficiently opaque, it is preferable for the enclosure 5 to be opaque, and preferably absorbent, so as to minimize parasitic reflections. The enclosure 5 may comprise a cover, provided that the latter is transparent. When the enclosure 5 is transparent, it is preferable for it to be placed on a translucent or opaque holder 6. Such a holder prevents parasitic reflections.

The device comprises a reflective element 13, for example a mirror, able to direct the incident light beam 12, emitted by the source, along an axis of incidence Z substantially perpendicular to the surface $3s$ of the object 3 to be observed, or substantially perpendicular to an XY plane, called the plane of the sample, in which the culture medium 4 of the sample 2 lies. By substantially perpendicular, what is meant is perpendicular to within an angular tolerance, the latter preferably being lower than ±30°, or preferably lower than ±20°. Thus, the incident light beam 12 reaches the object 3 at an angle of incidence substantially equal to 90°, to within the angular tolerance. In the shown example, the incident light beam comprises a first component $12_1$, between the light source 10 and the reflective element 13, and a second component $12_2$, between the reflective element 13 and the object 3. The incident beam 12 that reaches the object is preferably centered with respect to the object 3, in the plane XY of the sample.

Under the effect of the illumination by the incident beam 12, the object 3 emits back-scattered radiation 14 that propagates along or about a central back-propagation axis −Z that is parallel to the axis of incidence Z, and in the opposite direction to the latter. Generally, the term back-scattered radiation designates radiation that propagates along an propagation axis comprising a component opposite to the axis of incidence Z. The back-scattered radiation 14 results from the interaction of the photons of the incident beam 12 with the object 3, the latter having a refractive index higher than the refractive index of the ambient medium 7 through which the incident beam propagates, the ambient medium 7 generally being air. Because of the angle of incidence, most of the incident beam 12 penetrates into the object 3, thereby forming a refracted incident beam. The incident beam 12 refracted in the object 3 undergoes one or more elastic scatters in the object, and may generate diffraction waves. Back-scattered radiation 14 emanates from the object and propagates through the surface $3s$, as described with reference to FIGS. 1B and 1C. The back-scattered radiation is reflected in the ambient medium 7, then propagates, about the back-propagation axis −Z, to a screen 20, on which it forms an image $I_{20}$, called a scattergram, that is representative of the back-scattered radiation. The back-propagation axis −Z is coaxial to the axis of incidence Z along which the incident beam reaches the object. In the literature, the image referred to here as a scattergram is also termed a scattering pattern. It will be noted that no focusing or image-forming optic is placed between the object 3 and the screen 20.

The area of the reflective element 13 is the smallest possible, so as to not interfere with the back-scattered radiation 14 emanating from the object 3. It is preferably smaller than 5 cm², and even more preferably smaller than 2 cm², or even smaller than 1 cm². The area of the reflective element 13 is preferably suitable for the diameter of the beam emitted by the light source 10.

The screen 20 is able to collect the radiation 14 back scattered by the object 3 when it is illuminated by the light beam 12. The term screen designates an element a first face $20_1$ of which collects the back-scattered radiation 14, the latter being projected onto said first face $20_1$. Thus, the scattergram $I_{20}$ forms on the first face $20_1$ of the screen 20. The screen 20 has, in the XY plane of the sample, an area of at least 50 cm², but it is preferable for its area to be larger than 100 cm², or even larger than 200 cm², and for example of 400 cm², i.e. a square of 20 cm side length.

The device comprises an image sensor 30, in order to acquire an image $I_{30}$ of the scattergram $I_{20}$ formed on the screen. The image sensor 30 may in particular be a matrix-array sensor comprising pixels arranged in a matrix array, each pixel forming one elementary photodetector. The image sensor 30 is for example a CCD or CMOS sensor. The image sensor 30 is connected to a processor 40, for example a microprocessor, comprising a memory 42 in which image-processing instructions are stored, these instructions allowing the image acquired by the image sensor 30 to be analyzed with a view to characterizing the object 3. The processor 40 may also allow the holder 6 to be moved with respect to the screen 20, as explained below. A monitor 44 allows the acquired image to be viewed.

In the embodiment illustrated in FIG. 2A, in order to allow the scattergram to be projected onto the screen 20, the screen 20 is not completely transparent: it interacts with the scattered radiation 14, via absorption and/or scatter. Preferably, the screen transmits up to 80%, or even 90% or even 95% of the back-scattered radiation, the portion not transmitted being absorbed or scattered. The inventors believe that a transmittance of about 75% is optimal. By transmittance, what is meant is a ratio between an intensity of a radiation transmitted by the screen and an intensity of a radiation incident on the screen. The transmittance of the screen is preferably lower than 95%, or even lower than 90% or 80%. Opacity is defined as being the inverse of transmittance. The screen 20 comprises a second face $20_2$ that preferably lies parallel to the first face $20_1$. The screen 20 is configured such that the image projected onto the first face $20_1$, in the present case the scattergram, also appears, via transmission and/or scatter, on the second face $20_2$. The screen 20 then functions as a backlit screen, or a rear-projection screen, since it is interposed between the source of the scattered radiation, in the present case the object 3, and the image sensor 30. This screen 20 may be translucent, the term translucent designating a material that is not transparent, i.e. through which elements cannot be clearly distinguished, but that lets light pass. It is for example a tracing-paper substrate, a substrate comprising scattering elements, for example microspheres, or even a fabric or a sheet of roughened glass. When the screen comprises microspheres, they may be microspheres made of polycarbonate.

Rear-projection screens, taking the form of fabrics, suitable for this application are for example sold by Multivision under the references "retro gris" and "retro crème". When the screen 20 is a sheet of tracing paper, it may comprise a rough surface the Bendtsen roughness of which is 100 to 300 ml/mm, the Bendtsen roughness being determined according to standard NF 8791-2. The scattergram formed on the first face $20_1$ appears on the second face $20_2$, as shown in FIG. 2B.

The device comprises a focusing optic 25, allowing the scattergram $I_{20}$ formed on the second face $20_2$ of the screen 20, to be focused such that the image $I_{30}$ acquired by the image sensor corresponds to this scattergram. Preferably, the image sensor 30 lies parallel to the screen 20, and the focusing optic 25 comprises an optical axis that is coaxial with the back-propagation axis −Z (or with the axis of incidence Z). The image formed by the image sensor therefore corresponds to the scattergram $I_{20}$ formed on the screen, without deformation.

According to one variant, the screen 20 comprises a structured optical component, for example defining a Fresnel lens. A Fresnel lens comprises concentric annular structures arranged to focus an image of large diameter over a short focal length. The company DNP sells screens intended for back-scatter applications, based on one or both of the faces of the screen having optical lenses structured therein. These screens are referred to as optical rear-projection screens. Such screens allow the quantity of signal collected by the image sensor to be increased.

According to one variant, the screen 20 comprises a plurality of light guides extending between the first face $20_1$ and the second face $20_2$, in order to convey the scattergram from the first face $20_1$ to the second face $20_2$. It may be a question of a fiber-optic panel comprising an array of optical fibers extending, one beside the other, between the first face $20_1$ and the second face $20_2$. The size, in the XY plane, of such a screen may reach several hundred cm², for example 32.5 cm×32.5 cm. The diameter of each optical fiber is comprised between 5 μm and 25 μm, the numerical aperture being comprised between 0.92 and 1. Such panels are for example sold by Schott.

FIG. 2C shows a screen formed from two layers: a lower layer 21, defining the first face $20_1$ of the screen, and an upper layer 22 defining the second face of the screen $20_2$. The lower layer 21 may be scattering, for example because it consists of a roughened sheet made of glass or plastic, the roughened surface corresponding to the first face $20_1$. The upper layer 22 may form a Fresnel lens or a transparent sheet made of glass, playing the role of protective layer.

FIG. 2D shows a detail of the reflective element 13, and the incident radiation 12 and the back-scattered radiation 14. The incident radiation 12 comprises a first component $12_1$, which propagates between the light source 10 and the reflective element 13. It comprises a second component $12_2$ which propagates from the reflective element 13 to the object 3. The back-scattered radiation 14 emanating from the object 3, and which takes the form of a cone 15 of apex angle Ω has also been shown. It comprises a first component, denoted $14_1$, called the reflection component, corresponding essentially to specular reflection of the incident beam 12 from the surface of the sample, to which is added diffraction of order 0. It comprises a second component $14_2$, lying about the first component $14_1$, the second component containing information that may be used to characterize the object 3. The reflective element 13 is dimensioned depending on the diameter of the beam $12_1$ emitted by the light source. It is for example a question of a prism of 10 to 15 mm side length, which is inclined at 45° with respect to the orientation of the beam $12_1$ coming from the light source 10. It is preferable for the reflective element 13 to be securely fastened to the screen 20. This makes it possible to prevent an arm B, intended to hold the reflective element, from needing to extend into the cone 15 of propagation of the back-scattered radiation 14, as this would lead to a degradation of the scattergram formed on the screen 20. The distance δ between the reflective element 13 and the screen 20 is preferably larger than 1 mm. A too small distance δ, for example a distance smaller than 1 mm, may lead to an interaction of the laser beam $12_1$ emitted by the light source, and which propagates to the reflective element 13, with the screen 20. It is preferable for the distance δ to be smaller than 10 mm or 20 mm, or even 30 mm, so as not to hinder a translation of the sample 2 in the direction of the screen 20, as described below. The reflective element 13 will have preferably been given an anti-reflective treatment. The reflective element 13 may comprise an opaque rear surface 16, so as to block propagation of non-reflected radiation. This makes it possible to avoid leakage of light. The reflective element may be joined to the screen 20 by a binding medium 17. Preferably, the binding medium 17 extends, between the reflective element and the screen, parallel to the axis Z of the incident beam 12 that reaches the sample, while advantageously being coaxial to the incident beam 12 that reaches the sample.

Preferably, contrary to the device described in patent application WO2016/097063, the back-scattered radiation 14 propagating toward the screen 20 is blocked either by the reflective element 13, or by the binding medium 17. This blocks transmission of the first component $14_1$ (reflection component) of the radiation back scattered toward the screen. However, as indicated above, the reflection component $14_1$ essentially represents specular reflection of the incident beam 12 from the object 3; it contains no, or little, information that is useful with respect to characterizing the observed object 3. In addition, this first component is generally bright. Its non-transmission toward the screen 20 allows a bright and uninformative contribution to the scattergram to be blocked. This improves the dynamic range of the scattergram. The masking of the reflection component $14_1$ appears, in the scattergrams, in the form of a dark disk, the latter being a shadow of the reflective element 13, or of the binding medium 14. This shadow is indicated by a black arrow on the scattergram shown in FIG. 2B. Preferably, the reflective element 13 and/or the binding medium 17 absorb at least 30%, and advantageously at least 50%, or even 80% or 90% of the back-scattered radiation 14 emitted by the object. Their size is adjusted so that they mask only the reflection component $14_1$, and not the component $14_2$, of the back-scattered radiation, containing useful information.

The distance d between the sample 2 and the screen 20 is advantageously variable, as illustrated in FIGS. 2E and 2F. Specifically, as indicated above, the spatial distribution of the back-scattered radiation 14 may vary, the latter possibly taking the form of a cone 15 of relative openness extending divergently or convergently from the object. Thus, the holder 6 of the sample may be mounted on a translatable stage that permits a translation parallel to the axis of incidence Z. FIGS. 2E and 2F show a sample 2 located at a first distance $d=d_1$ and at a second distance $d=d_2$ from the screen 20, with $d_1>d_2$. The movement of the holder 6 may be controlled by the processor 40. The range of variation in the distance is typically 3 cm to 20 cm, or even 30 cm. The distance is determined depending on the scattergram formed on the screen 20, so that the scattergram extends over the largest possible area, while remaining compatible with the field of view of the image sensor 30, the latter depending on the size of the image sensor 30 and of the focusing optical system 25.

The distance may be adjusted manually, or by implementing an algorithm based on recognition of the outline bounding the scattergram. Such an algorithm may for example use a Canny filter. When this outline has been detected, the distance is adjusted so as to make the area of the scattergram, on the screen 20, exceed a preset threshold value. The adjustment of the distance d makes it possible to take into account the variability in the back-scattered radiation due to the various types of objects to be characterized. According to one embodiment, once an optimal distance has been determined, allowing the area of the scattergram projected onto the screen to be maximized, an image of the scattergram is acquired. The distance is then increased, so as to verify the absence of back-scattered radiation outside of the scattergram observed beforehand, i.e. that corresponding to the optimal distance.

Preferably, the holder 6 is also movable in the XY plane of the sample. This allows the incident light beam 12 to be centered on the object 3. This allows an analysis to be carried out whatever the position of the object 3 in the sample 2. Such centering may be adjusted depending on a symmetry criterion of the scattergram. Specifically, when the incident beam is centered on the object, the scattergram present on the screen has a symmetry of revolution. The symmetry may for example be quantified via the shape of the outline of the scattergram.

Figure 3A:
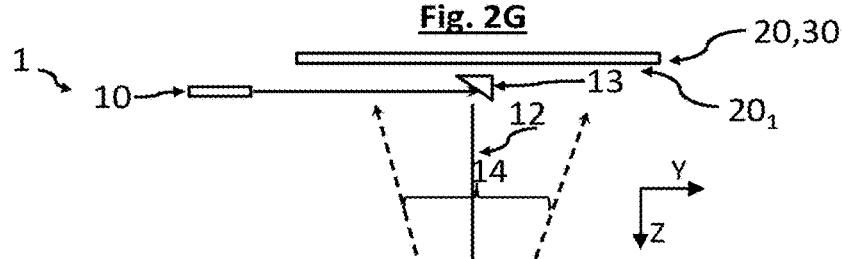
FIGS. 3A and 3B illustrate a second embodiment and a third embodiment, respectively.

According to a second embodiment, shown in FIG. 3A, the screen 20 is formed by an image sensor of large size, the sensitive area of which is larger than 100 cm$^2$ or indeed more. According to this embodiment, the screen 20 also plays the role of image sensor 30. The image sensor may be a sensor such as used in medical x-ray imaging devices, it then being coupled to a scintillator material ensuring a conversion between the x-ray radiation and visible radiation detectable by the image sensor. This type of sensor is sensitive to visible radiation, while having an area that may be large. The screen 20 corresponds to a photosensitive portion of the image sensor 30, in which portion incident visible photons are converted into charge carriers.

An example of manufacture of such a sensor made of silicon, the detection area of which is larger than 100 cm$^2$, or even 200 cm$^2$, is given in document WO2014/006214. The area of the pixels may be comprised between 50 μm$^2$ and 200 μm$^2$. A transparent protective panel of small thickness, typically a few millimeters in thickness, may be placed against the screen 20. Such an embodiment may allow a significant improvement in sensitivity with respect to the first embodiment, its cost however being higher.

Figure 3B:
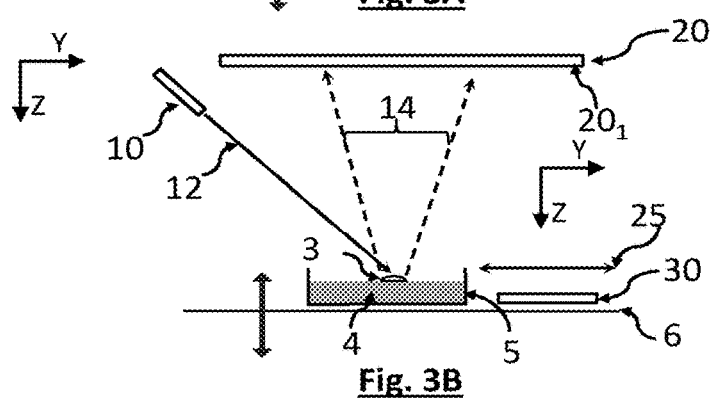

According to a second embodiment, shown in FIG. 3B, the screen 20 is not a rear-projection screen, but a front-projection screen, the sample 2 and the image sensor 30 being placed facing the same face of the screen 20. In this embodiment, the back-scattered radiation 14 forms a scattergram on the first face of the screen $20_1$. The image sensor 30 is optically coupled to the first face $20_1$, using an optical system 25. The image sensor 30 acquires an image of the scattergram projected onto the first face. However, in this embodiment, the image sensor is off-center with respect to the screen. In this embodiment, it is not possible to remove the reflection component $14_1$ of the scattergram formed on the screen 20. In addition, this embodiment does not allow both the screen 20 and the incident light beam 12 to be centered on the object 3 to be characterized.

Figure 3C:
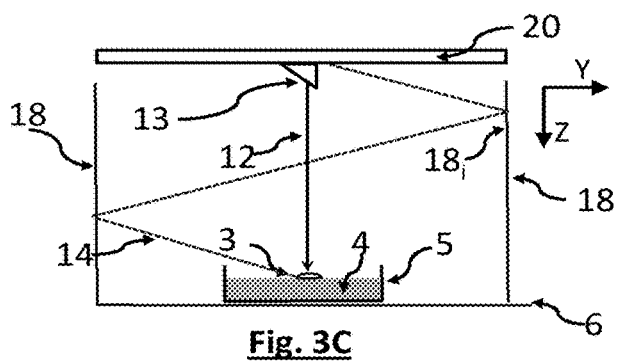
FIGS. 3C and 3D show variants applicable to all the embodiments.
Figure 3D:
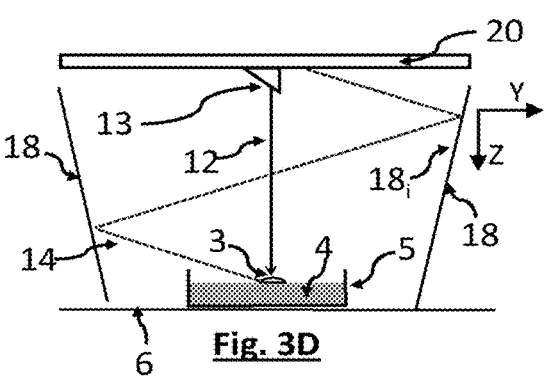

The spatial distribution of the back-scattered radiation 14 may vary significantly depending on the observed object. In certain cases, it extends over a very high angular range on either side of the axis of incidence Z. This is in particular case when the object, in the present case a bacterial colony, has a curved morphology, such a morphology for example being observed in bacterial colonies of *Staphylococcus*. In such a case, the size of the screen 20 must be large in order to obtain a complete scattergram, in particular taking into account large back-scatter angles (typically larger than 65°). The expression "back-scatter angle" is understood to mean the angle between back-scattered radiation 14 emanating from the object and the axis of incidence Z. It is also possible to adjust the distance between the screen 20 and the object 3, as indicated above. This notably allows a scattergram the diameter of which corresponds to a preset template, for example a diameter comprised between 15 and 20 cm, to be obtained. FIG. 3C describes a variant allowing a reasonable size to be preserved for the screen 20 while allowing back-scattered radiation 14 emanating from the object at large back-scatter angles to be taken into account. According to this variant, an annular reflector 18, extending parallel to the axis of incidence Z, is placed between the object 3 and the screen 20, around all or some of the object 3. The annular reflector 18 allows some of the radiation 14 back scattered toward the screen 20 to be reflected. It may be a question of a tubular reflector that is coaxial with the axis of incidence Z. FIG. 3C shows a cylindrical annular reflector. Its height and its diameter may be 6 cm and 17.5 cm, respectively. It may be a question of a cylinder the internal wall 18$i$ of which is reflective. For example, a thin metal layer, for example of aluminum, may have been deposited on the internal wall 18$i$. The annular reflector 18 may also be of conical shape, as shown in FIG. 3D. Such a conical reflector may have a small diameter equal to 19 cm, a large diameter equal to 20 cm, and a height of 3 cm. The angle of inclination of the internal wall, with respect to the axis Z, is for example 13°. The angle of the internal wall 18$i$ may be dimensioned such that the back-scattered radiation 14 having the largest back-scatter angle undergoes only a single reflection before reaching the screen 20. Preferably, at least one diameter of the annular reflector 18 is larger than two times the diameter of the enclosure 5.

A space may be left between the annular reflector 18 and the screen 20, so as to allow the incident light beam 12 to propagate between the light source 10 and the reflective element 13.

FIG. 3E shows a variant in which the screen 20 is not planar and has a curved shape that curves toward the sample 2. This also facilitates a collection, by the screen, of radiation back scattered at large back-scatter angles. The curvature of the screen 20 may be regular or not. The screen 20 may for example describe all or part of a hemisphere. The screen 20 may have a dome shape. The screen may also describe a curvature having planar facets. By curving toward the sample, what is meant is that the screen describes a curvature the center of which is comprised between the sample and the screen, or, more generally, the center of which is located in a half-space bounded by the screen and comprising the sample. Thus, the screen has a concave shape, so as to define a space lying between the screen and the sample, this space being such that, whatever two points of said space are considered, the segment connecting said points is included in the space. It is for example possible to use a dome-shaped ¼" custom vacuum formed acrylic IRUS screen with a Cine25 tint and an HC coating as sold by Draper Inc. Preferably, the reflective element is placed in proximity to the first face $20_1$ of the screen, at the apex of the screen 20.

Figure 2G:
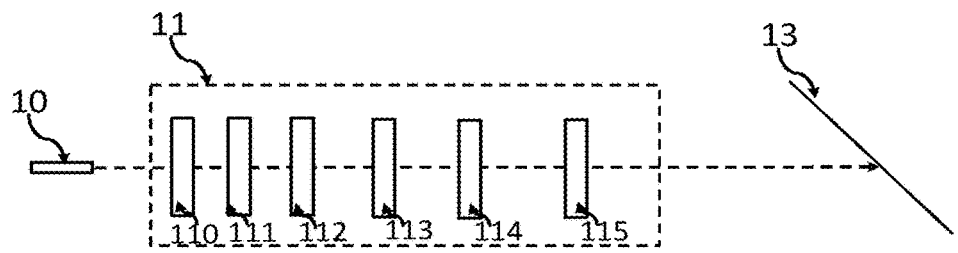
FIG. 2G is an example of an optical system for shaping the laser beam.

Whatever the embodiment, a forming optical system 11 may be associated with the light source 10, so as to form a collimated incident beam 12, according to principles known to those skilled in the art. FIG. 2G shows an example of a forming optical system. It comprises a succession of conventional optical components: an achromatic lens 110, a pinhole 111 of 50 µm diameter, a convergent lens 112 and a beam expander 113. The forming optical system 11 may comprise, optionally, a flat-top beam converter 114 followed by a beam reducer 115. The beam expander 113 allows the size of the laser beam to be adjusted, so that the latter approaches the size of the object to be observed. The expander 113 may consist of a set of two lenses of variable focal length, which is programmable by the processor 40. The beam converter 114 allows the distribution of the intensity in the beam to be adjusted.

The image obtained on the image sensor 20 may allow the object 3 to be characterized. The characterization may be an identification. To this end, characteristics of the image are determined, and compared to calibration characteristics established on standard objects. These characteristics may also be the subject of a classification on the basis of said calibration characteristics. Patent application WO2014184390 describes a method for classifying bacterial colonies based on a projection of the image onto a basis of orthogonal Zernike polynomials. Other classifying algorithms, for example allowing a principal-component analysis to be obtained, are envisionable. The objective of such a classification is to decrease the spatial information in the image into a set of coordinates, on the basis of which the identification of the microorganism is obtained.

Since the method is nondestructive, a plurality of images of a given bacterial colony, at various stages of incubation, may be produced, so as to assess the propensity of the colony to develop, or its ability to resist an antibiotic or antibacterial agent. In this case, the characterization of the object represents the tendency of the latter to develop.

The method may also allow the number of objects present on the surface of a sample to be counted.

Experimental Trials

Experimental trials that were carried out using the first embodiment will now be described. The main components used were the following:
- light source 10: laser source of reference LCG FP-D-532-10C-F—supplied by Laser components.
- Forming optical system 11: achromatic lens Thorlabs AC254-030-A-ML—A280TM-A, pinhole Thorlabs—P50 S, convergent lens Thorlabs A280TM-A.
- Sample enclosure: petri dish of 90 mm diameter—Biomérieux.
- Translucent screen: Luminit L80P3-12 polycarbonate diffuser, or tracing paper.
- Focusing optical system: LM5JC10M—Kowa.
- Camera: UI-1492ME—IDS or AVGT3300—Allied Vision.
- Reflective element: mirror inclined at 45°.
- The assembly is placed in the dark.

During these trials, various types of bacterial colonies were observed. During each operation, the incident laser beam 12 was centered on the colony visually, by the operator. The exposure time of each acquired image was comprised between 0.6 ms and 1500 ms. Certain images were obtained by summing various images acquired by the image sensor.

FIGS. 4A and 4B show a scattergram of an *Escherichia coli* bacterial colony on a Columbia blood agar (CBA) culture medium. The screen used was a piece of tracing paper. The reflective element 13 was supported either by a transverse arm B extending parallel to the screen 20 (FIG. 4A), or by a holder 17 fastened to the screen (FIG. 4B), as shown in FIG. 2D. In FIG. 4A, it may be seen that the transverse arm B, which extends parallel to the screen 20, blocks the back-scattered radiation 14, this producing a dark rectilinear shadow in the scattergram. It may also be seen that the scattergram comprises a bright central zone, saturating the pixels of the image sensor, which corresponds to the reflection component $14_1$ described above. In FIG. 4B, a central circular dark spot, which is formed by the shadow of the holder 17, and which is indicated by an arrow, may be seen. This shadow masks the reflection component $14_1$. Therefore, the dynamic range of the image is optimized, and the peripheral zone $14_2$ of the scattergram appears more clearly. These images justify the arrangement of the reflective element 13 described with reference to FIG. 2D.

FIGS. 5A to 5C illustrate a method for centering the object 3 with respect to the incident beam 12 and with respect to the screen. FIG. 5A is an image of a scattergram of a bacterial colony of *Escherichia aerogenes*, on a CBA culture medium, the screen used being a piece of tracing paper. By applying a Canny filter to detect edges, FIG. 5B was obtained. The diameter of the scattergram was estimated to be 8.2 cm. The center of the scattergram was determined, and the sample was moved so that the center of the scattergram was placed at the center of the image acquired by the image sensor (FIG. 5C). This allows the colony to be aligned with the incident beam 12 and with the optical axis of the image sensor.

FIG. 6 is an image, said to be of high-dynamic range, obtained by acquiring 11 images of the same scattergram, the exposure time varying between 8 ms and 495 ms. A high-dynamic range (HDR) algorithm was implemented to combine the acquired images and to form the image of FIG. 6. This image shows a bacterial colony of *Staphylococcus epidermidis* on a CBA culture medium, the screen being a piece of tracing paper.

Figure 7A:
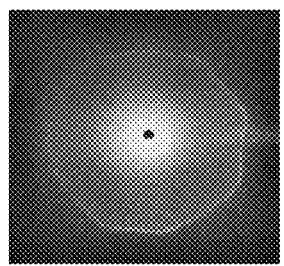
Figure 7B:
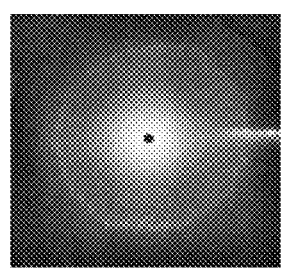
Figure 7C:
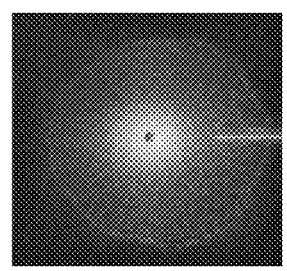
Figure 7D:
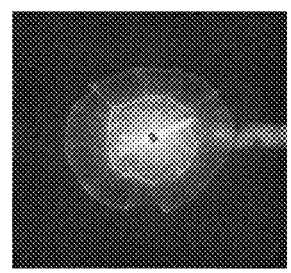
Figure 7E:
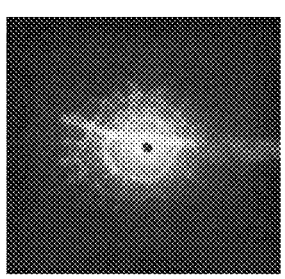
Figure 7F:
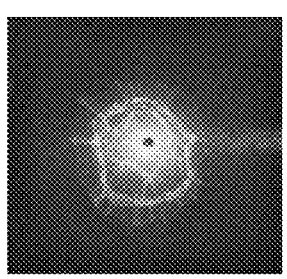

FIGS. 7A to 7F are examples of images of scattergrams obtained by observing bacterial colonies developing on a CBA agar such as described above. Each scattergram was 20 cm×20 cm in size. The screen used to obtain these scattergrams was a piece of tracing paper. The parameters of each figure are now listed:
FIG. 7A: *Staphylococcus warneri*—diameter of the laser beam: 900 µm;
FIG. 7B: *Staphylococcus saprophyticus*—diameter of the laser beam: 900 µm;
FIG. 7C: *Staphylococcus epidermidis*—diameter of the laser beam: 900 µm;
FIG. 7D: *Escherichia coli*—diameter of the laser beam: 1800 µm;
FIG. 7E: *Pseudomonas putida*—diameter of the laser beam: 2800 µm;
FIG. 7F: *Enterobacter cloacae*—diameter of the laser beam: 2800 µm.

FIGS. 8A to 8D show observations of colonies of various sizes. FIG. 8A shows a microscope observation of a microcolony of *Staphylococcus epidermidis* of 760 µm diameter. FIG. 8B shows a scattergram of this microcolony. FIG. 8C shows a microscope observation of a microcolony of *Escherichia coli* of 1160 µm diameter. FIG. 8D shows a scattergram of this microcolony.

FIGS. 9A to 9C show scattergrams obtained on various agars:

FIG. 9A shows a scattergram of *Staphylococcus saprophyticus* on a PolyViteX chocolate agar (PVX);

FIG. 9B shows a scattergram of *Pseudomonas putida* on a Mueller-Hinton agar;

FIG. 9C shows a scattergram of *Escherichia coli* on a trypticase soy agar (TSA).

These figures illustrate the compatibility of the invention with various culture media 4, whether they are opaque (CBA, PVX) or transparent (TSA).

FIG. 9D shows a scattergram of a colony of *Staphylococcus saprophyticus* developing on a surface formed by a lawn of *Pseudomonas putida*. This result shows that the invention allows nondestructive observation of a colony in situ, without having to take a sample.

The observing method of the invention is nondestructive and may be applied directly to a colony, in its culture medium. This allows a progression of the development of a colony to be observed. FIG. 10 shows the change over time in a scattergram of the same colony of *Staphylococcus epidermidis* on a CBA medium. Each image of this figure is a scattergram of the colony, the time interval between two successive images being 1 h. The first image (at the top left) corresponds to an incubation time of 16 h, the last image (at the bottom right) corresponding to an incubation time of 24 h. The incubation time is mentioned at the top right of each image.

FIG. 11A shows an experimental device used in a trial to compare an image obtained with a flat screen with an image obtained with a dome-shaped screen, such as described with reference to FIG. 3E. The screen 20 comprised a curved portion 20a and a flat portion 20b. The curved portion 20a was a portion of a hemisphere of frosted glass. The planar portion 20b was formed by a piece of tracing paper. A trial was carried out, using a bacterial colony of *Pseudononas putida*, on a TSA agar. The scattergram obtained is shown in FIG. 11B. It may be seen that the scattergram overflows on the planar tracing paper, but is contained on the dome.

The invention will possibly be implemented to assist with various types of examinations, such as sterility tests, antibiotic susceptibility tests, antibacterial or bacteriophage susceptibility tests, to target antibacterial substances, for identification purposes, or for counting purposes. The invention may also be applied to the observation and characterization of other types of microorganisms, such as yeast, fungi, or microalgaes.

The invention claimed is:

1. A device for observing an object, within a sample, comprising:
    a holder, configured to hold the sample, the holder defining a sample plane, in which the sample lies when the sample is placed on the holder;
    a light source, configured to emit an incident light beam, in order to illuminate the object;
    an image sensor, configured to acquire an image representative of a radiation back scattered by the object when illuminated by the incident light beam;
    a screen, lying facing the holder, so as to be exposed to the radiation back scattered by the object when the object is illuminated by the incident light beam, so as to form, on the screen, a scattergram, the scattergram being the image representative of the back-scattered radiation;
    the screen comprising a first face exposed to the back-scattered radiation, the area of the first face being larger than 100 cm$^2$;
    the image sensor being configured to acquire an image of the scattergram formed on the screen;
    the device further comprising a reflective element, placed between the screen and the object, the reflective element being configured to reflect a portion of the incident light beam along an axis of incidence perpendicular or substantially perpendicular to the sample plane, the reflective element being securely fastened to the first face of the screen;
    the device further comprising a binding medium lying between the reflective element and the screen, the binding medium allowing the reflective element to be fastened to the screen;
    wherein the reflective element and/or the binding medium are configured to absorb at least 50% of the back-scattered radiation propagating between the object and the screen; and
    wherein the screen, the reflective element, and the object are aligned along the axis of incidence.

2. The device of claim 1, wherein the screen is curved.

3. The device of claim 1, wherein:
    the screen comprises a second face, so that the scattergram formed on the first face appears on the second face;
    the screen lies between the image sensor and the holder, in such a way that the image sensor is coupled to the second face by a focusing optic.

4. The device of claim 3, wherein the screen transmits less than 90% of the back-scattered radiation between the first face and the second face.

5. The device as claimed in claim 3, wherein the screen is movable with respect to the holder, a distance between the holder and the screen being adjustable.

6. The device of claim 1, wherein a distance between the reflective element and the screen is smaller than 2 cm.

7. The device of claim 1, wherein the area of the reflective element is smaller than 4 cm$^2$.

8. The device of claim 3, wherein:
    the screen is translucent; and/or
    the screen comprises a light guide for conveying light between the first face and the second face; and/or
    the screen comprises a plurality of optical fibers extending between the first face and the second face.

9. The device of claim 1, wherein the screen is a photosensitive portion of the image sensor.

10. The device of claim 1, wherein the incident light beam propagates between the reflective element and the object along the axis of incidence, the device comprising an annular reflector, lying around the axis of incidence, between the sample and the screen, the reflector being configured to reflect some of the radiation back scattered toward the screen.

11. A method for observing an object present in a sample, the sample lying facing a screen, the screen comprising a first face, the method comprising:
    a) illuminating the object using an incident light beam, emitted by a light source, the incident light beam propagating to a reflective element placed between the screen and the object, the reflective element directing all or some of the incident light beam toward the object, the reflective element being joined to the first face of the screen;
    b) exposing the first face of the screen to a light radiation back scattered by the sample under the illumination, so as to form, on the first face, a scattergram, representative of the back-scattered radiation, the area of the first face being larger than 100 cm$^2$;

c) acquiring an image of the scattergram formed on the screen with an image sensor;

wherein:

the incident light beam propagates from the reflective element to the object along an axis of incidence;

the back-scattered radiation propagating toward the screen, along the axis of incidence, is absorbed before reaching the screen, so as to form a shadow in the scattergram formed on the screen; and the screen, the reflective element, and the object are aligned with respect to the axis of incidence.

12. The method of claim 11, wherein the area of the reflective element is smaller than 5 cm$^2$.

13. The method of claim 11, wherein a distance between the reflective element and the screen is smaller than 1 cm.

14. The method of claim 11, wherein the screen comprises a second face, the screen lying between the image sensor and the sample so that the image sensor is optically coupled to the second face via a focusing optic, the screen being such that the scattergram formed on the first face appears on the second face.

15. The method of claim 14, wherein:

the screen is curved; and/or the screen is translucent; and/or the screen comprises at least one optical fiber, extending between the first face and the second face; and/or one of the first face or the second face of the screen is structured so as to form a lens.

16. The method of claim 15, wherein the screen transmits less than 90% of the back-scattered radiation from the first face to the second face.

17. The method of claim 11, wherein the screen is a photosensitive portion of the image sensor.

18. The method of claim 11, comprising, following c):

adjusting a distance between the sample and the screen depending on the image acquired by the image sensor;

repeating a) to c) after the adjustment of the distance between the sample and the screen.

19. The method of claim 11, comprising:

d) characterizing the object on the basis of the image acquired by the image sensor.

20. The method of claim 19, wherein d) further comprises:

determining characteristics of the image;

identifying the object using the characteristics and calibration characteristics established by implementing a) to c) of the method on a standard sample.

21. The method of claim 11, wherein the object comprises a microorganism.

* * * * *